(12) United States Patent
Su et al.

(10) Patent No.: US 10,451,492 B2
(45) Date of Patent: Oct. 22, 2019

(54) ZERO-STRAIN SOIL PRESSURE SENSOR

(71) Applicant: SHENZHEN UNIVERSITY, Guangdong (CN)

(72) Inventors: Dong Su, Guangdong (CN); Yueqin Jiang, Guangdong (CN); Xiaohua Bao, Guangdong (CN); Zhongliang Yu, Guangdong (CN)

(73) Assignee: SHENZHEN UNIVERSITY, Guangdong (CN)

( * ) Notice: Subject to any disclaimer, the term of this patent is extended or adjusted under 35 U.S.C. 154(b) by 33 days.

(21) Appl. No.: 15/771,386

(22) PCT Filed: Mar. 30, 2016

(86) PCT No.: PCT/CN2016/077926
§ 371 (c)(1),
(2) Date: Apr. 26, 2018

(87) PCT Pub. No.: WO2017/084232
PCT Pub. Date: May 26, 2017

(65) Prior Publication Data
US 2018/0306653 A1 Oct. 25, 2018

(30) Foreign Application Priority Data
Nov. 20, 2015 (CN) .......................... 2015 1 0810591

(51) Int. Cl.
*G01L 1/08* (2006.01)
*G01L 1/02* (2006.01)
*G01N 33/24* (2006.01)

(52) U.S. Cl.
CPC ................ *G01L 1/083* (2013.01); *G01L 1/02* (2013.01); *G01L 1/08* (2013.01); *G01N 33/24* (2013.01)

(58) Field of Classification Search
CPC .. G01L 1/083; G01L 1/02; G01L 1/08; G01N 33/24
(Continued)

(56) References Cited

U.S. PATENT DOCUMENTS

| | | | | |
|---|---|---|---|---|
| 1,085,501 | A | * | 10/1967 | Thomas .................. F16H 37/08 74/366 |
| 8,827,001 | B2 | * | 9/2014 | Wendte ................ A01B 63/008 172/4 |

FOREIGN PATENT DOCUMENTS

| | | |
|---|---|---|
| CN | 1987385 | 6/2007 |
| CN | 102519630 | * 6/2012 |

(Continued)

OTHER PUBLICATIONS

"International Search Report (Form PCT/ISA/210)", dated Jul. 26, 2016, with English translation thereof pp. 1-5.

*Primary Examiner* — Octavia Hollington
(74) *Attorney, Agent, or Firm* — JCIPRNET

(57) ABSTRACT

A zero-strain soil pressure sensor includes a shell provided with a hydraulic oil cavity and a cavity located below the hydraulic oil cavity, a processor, an outer elastic film arranged at the upper end of the hydraulic oil cavity, an inner elastic film arranged between the hydraulic oil cavity and the cavity, an outer strain bridge circuit connected with the outer elastic film, an inner strain bridge circuit connected with the inner elastic film, a piston communicated with the hydraulic oil cavity, and a driving mechanism connected with the piston. The outer strain bridge circuit, the inner strain bridge circuit and the driving mechanism are electrically connected with the processor. The invention has the beneficial effect that the piston is driven by the driving mechanism to control the oil pressure in the hydraulic oil cavity, external soil pressure is balanced through the oil pressure to keep the outer elastic film in an non-deforming state all the time, and (Continued)

only the inner elastic film is deformed, so that the soil arch effect and soil displacement are avoided, and thus the liquid pressure measured by the inner elastic film is the soil pressure, and the measurement result is more accurate.

5 Claims, 2 Drawing Sheets

(58) Field of Classification Search
USPC .......................................................... 73/784
See application file for complete search history.

(56) References Cited

FOREIGN PATENT DOCUMENTS

| | | |
|---|---|---|
| CN | 202403841 | 8/2012 |
| CN | 104266790 | 1/2015 |
| CN | 105300570 | 2/2016 |
| CN | 205209663 | 5/2016 |
| DE | 102012222108 | 6/2014 |
| EP | 0974820 | 1/2000 |

* cited by examiner

ZERO-STRAIN SOIL PRESSURE SENSOR

CROSS-REFERENCE TO RELATED APPLICATION

This application is a 371 application of the international PCT application serial no. PCT/CN2016/077926, filed on Mar. 30, 2016, which claims the priority benefit of China application no. 201510810591.3, filed on Nov. 20, 2015. The entirety of each of the abovementioned patent applications is hereby incorporated by reference herein and made a part of this specification.

BACKGROUND

Technical Field

The invention relates to the field of soil pressure measurement, in particular to a zero-strain soil pressure sensor.

Description of Related Art

Zero-strain soil pressure sensors are test tools used for measuring the ground stress of field soil. At present, the method of converting a non-electric quantity (pressure) into an electric quantity is mainly used for testing. As for the zero-strain soil pressure sensors, in most cases, sensor structures need to be embedded into soil media to make sensors and the soil media deform compatibly, structural deformation (strain) is the main test quantity and is mainly converted into an electric quantity such as inductance, capacitance, resistance, frequency and electric charge, and thus the zero-strain soil pressure sensors are mainly of a piezoelectric type, a vibrating wire type, an inductance type, a capacitance type, a resistance type and the like. Vibrating wire sensors and resistance sensors are most widely used currently, and the test quantities are the frequency and voltage respectively. As for the principle of the resistance sensors, structural physical quantities are converted into measurable electric quantities according to the relation between the resistance and structural changes of a metal wire (sheet). As for the vibrating type sensors, a steel wire and the sensor structure deform compatibly, and the magnitude of stress on the wire is induced through vibration of the steel wire under electromagnetic excitation. Piezoelectric crystal sensors are dynamic stress test sensors having broad prospects. When a specific side of a piezoelectric crystal is loaded, electric charges can be generated on the vertical surface of the piezoelectric crystal, and the electric charges disappear after the piezoelectric crystal is unloaded.

Most zero-strain soil pressure sensors used currently are provided with only one elastic film which can deform due to external pressure changes in the measurement process, the soil arch effect or soil displacement can be caused by deformation of the elastic film, resulting in changes of local soil pressure, and consequentially, significant measurement errors are generated. A double-film zero-strain soil pressure sensor is also adopted; however, in the measurement process, deformation of the first film can be caused when the second film deforms, and consequentially, the soil arch effect or soil displacement cannot be completely eliminated, and measurement errors are still generated.

SUMMARY OF THE INVENTION

To solve the problems in the prior art, the invention provides a zero-strain soil pressure sensor capable of achieving more accurate measurement.

The invention provides a zero-strain soil pressure sensor comprises a shell provided with a hydraulic oil cavity and a cavity located below the hydraulic oil cavity, a processor, an outer elastic film arranged at the upper end of the hydraulic oil cavity, an inner elastic film arranged between the hydraulic oil cavity and the cavity, an outer strain bridge circuit connected with the outer elastic film, an inner strain bridge circuit connected with the inner elastic film, a piston communicated with the hydraulic oil cavity, and a driving mechanism connected with the piston. The outer strain bridge circuit, the inner strain bridge circuit and the driving mechanism are all electrically connected with the processor.

As a further improvement of the invention, the driving mechanism comprises a stepping motor and a connecting rod, and the piston is connected with the stepping motor through the connecting rod.

As a further improvement of the invention, the processor is a single-chip microcomputer.

As a further improvement of the invention, a pressurization cavity is formed in one side of the hydraulic oil cavity and communicated with the hydraulic oil cavity, the cross section of the pressurization cavity is smaller than that of the hydraulic oil cavity, and the piston is arranged in the pressurization cavity.

As a further improvement of the invention, the processor is arranged in the cavity.

Beneficial effects of the invention are: the piston is driven by the driving mechanism to control the oil pressure in the hydraulic oil cavity, external soil pressure is balanced through the oil pressure to keep the outer elastic film in an non-deforming state all the time, and only the inner elastic film is deformed, so that the soil arch effect and soil displacement are avoided, and thus the liquid pressure measured by the inner elastic film is the soil pressure, and the measurement result is more accurate.

DETAILED DESCRIPTION OF THE EMBODIMENTS

Marks in the FIGs.: 1—shell; 2—processor; 3—outer elastic film; 4—inner elastic film; 5—hydraulic oil cavity; 6—cavity; 7—piston; 8—pressurization cavity; 9—stepping motor; 10—connecting rod; 11—wire a; 12—wire b; 13—wire c; 14—wire d; 31—outer strain bridge circuit; 41—inner strain bridge circuit.

Figure 1:
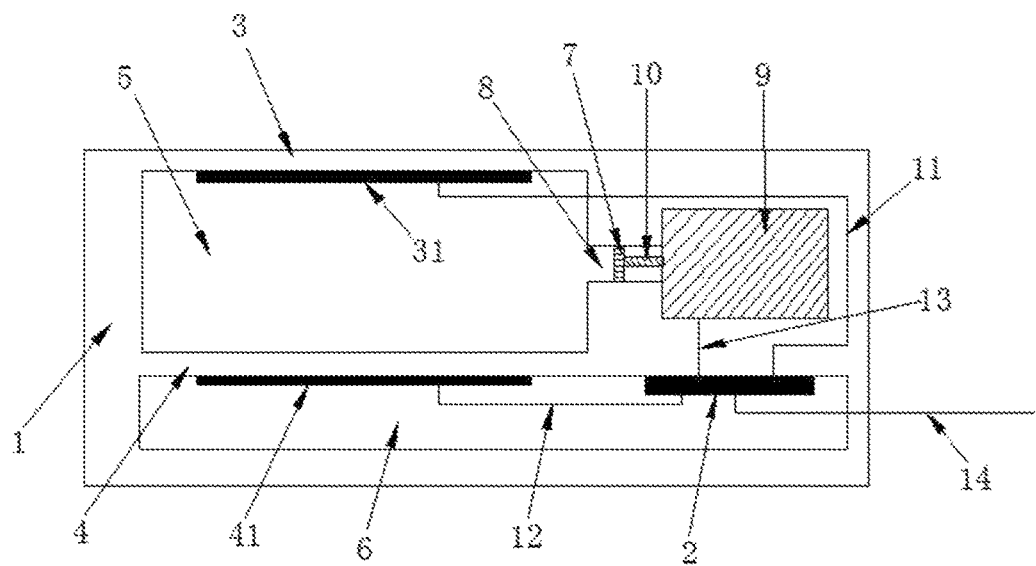
FIG. 1 is a structural diagram of a zero-strain soil pressure sensor of the invention.
Figure 2:
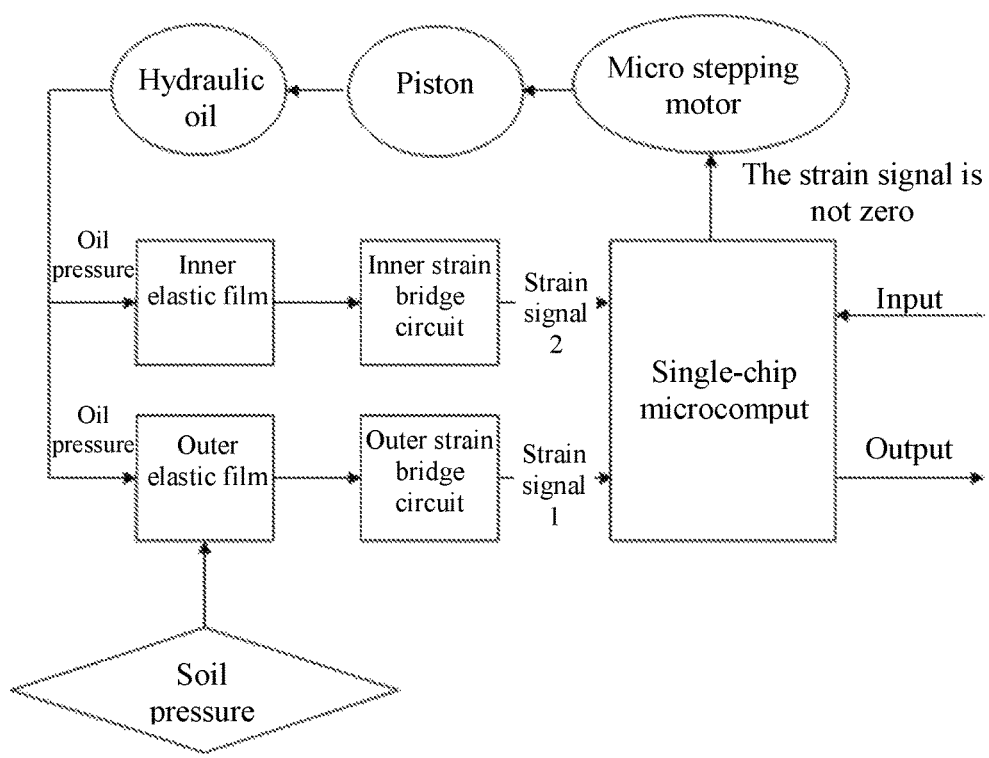
FIG. 2 is a block diagram of the operating principle of the zero-strain soil pressure sensor of the invention.

As is shown in FIG. 1 and FIG. 2, the invention provides a zero-strain soil pressure sensor. The zero-strain soil pressure sensor comprises a shell 1, a processor 2, an outer elastic film 3, an inner elastic film 4, an outer strain bridge circuit 31, an inner strain bridge circuit 41, a piston 7 and a driving mechanism. The shell 1 is provided with a hydraulic oil cavity 5 and a cavity 6 located below the hydraulic oil cavity 5. The outer elastic film 3 is arranged at the upper end of the hydraulic oil cavity 5 and located on the surface of the shell 1 and directly makes contact with soil. The inner elastic film 4 is arranged between the hydraulic oil cavity 5 and the cavity 6. The outer strain bridge circuit 31 is arranged at the lower end of the outer elastic film 3. The inner strain bridge circuit 41 is arranged at the lower end of the inner elastic film 4. The hydraulic oil cavity 5 is filled with hydraulic oil.

The piston 7 is connected with the driving mechanism and arranged in the hydraulic oil cavity 5. The driving mechanism can squeeze hydraulic oil in the hydraulic oil cavity 5 through the piston 7. The outer strain bridge circuit 31, the inner strain bridge circuit 41 and the driving mechanism are all electrically connected with the processor 2.

The driving mechanism comprises a stepping motor 9 and a connecting rod 10. The piston 7 is connected with the stepping motor 9 through the connecting rod 10. In the embodiment, the stepping motor 9 is a micro stepping motor and is more accurate in control. In certain embodiments, the driving mechanism is a driving cylinder, and driving the piston 7 to move by the driving cylinder can also achieve the effect of squeezing hydraulic oil.

In the embodiment, a pressurization cavity 8 is formed in one side of the hydraulic oil cavity 5 and communicated with the hydraulic oil cavity 5. The other side of the pressurization cavity 8 is communicated with a driving cavity. The stepping motor 9 is arranged in the driving cavity. The cross section of the pressurization cavity 8 is smaller than that of the hydraulic oil cavity 5. The piston 7 is arranged in the pressurization cavity 8. In this way, hydraulic oil is compressed in the pressurization cavity 8 and thus is easier to control, and the squeezing pressure is more accurate.

In the embodiment, the processor 2 is a single-chip microcomputer which is good in controllability, reliable, durable and low in cost.

In the embodiment, the processor 2 is arranged in the cavity.

The outer strain bridge circuit 31 is connected with the processor 2 through a wire a 11. The stepping motor 9 is connected with the processor 2 through a wire b 12. The inner strain bridge circuit 41 is connected with the processor 2 through a wire c 13. The processor 2 is connected with a power supply and outputs a signal through a wire d 14.

When external soil pressure is applied to the soil pressure sensor, the outer elastic film 3 is strained, the outer strain bridge circuit 31 detects the strain and sends a signal to the single-chip microcomputer 2, if the strain signal is not zero or exceed a preset threshold, the single-chip microcomputer 2 sends out a work instruction to the stepping motor 9, the stepping motor 9 pushes the piston 7 to move through the connecting rod 10, and hydraulic oil is then squeezed till the outer elastic film 3 is in an non-deforming state. In this way, the oil pressure in the hydraulic oil cavity 5 and the external soil pressure are kept balanced, the inner elastic film 4 is deformed under the effect of the oil pressure, the inner strain bridge circuit 41 detects the strain and sends a signal to the single-chip microcomputer 2, and the pressure corresponding to the signal is the soil pressure measured.

According to the invention, based on the feedback control principle, the piston is driven by the driving mechanism to control the oil pressure in the hydraulic oil cavity, the external soil pressure is balanced through the oil pressure to keep the outer elastic film 3 in an non-deforming state all the time, and only the inner elastic film 4 is deformed, so that the soil arch effect and soil displacement are avoided, and thus the liquid pressure measured by the inner elastic film 4 is the soil pressure, and the measurement result is more accurate.

A further detailed description of the invention is given above with preferred specific embodiments, but specific implementation of the invention is not limited to the above description. For those ordinarily skilled in the technical field, various simple deductions or substitutes can be made without deviating from the concept of the invention, and all these deductions or substitutes are within the protection scope of the invention.

What is claimed is:

1. A zero-strain soil pressure sensor, comprising a shell provided with a hydraulic oil cavity and a cavity located below the hydraulic oil cavity, a processor, an outer elastic film arranged at an upper end of the hydraulic oil cavity, an inner elastic film arranged between the hydraulic oil cavity and the cavity, an outer strain bridge circuit connected with the outer elastic film, an inner strain bridge circuit connected with the inner elastic film, a piston communicated with the hydraulic oil cavity, and a driving mechanism connected with the piston, wherein the outer strain bridge circuit, the inner strain bridge circuit and the driving mechanism are all electrically connected with the processor.

2. The zero-strain soil pressure sensor according to claim 1, wherein the driving mechanism comprises a stepping motor and a connecting rod, and the piston is connected with the stepping motor through the connecting rod.

3. The zero-strain soil pressure sensor according to claim 1, wherein the processor is a single-chip microcomputer.

4. The zero-strain soil pressure sensor according to claim 1, wherein a pressurization cavity is formed in one side of the hydraulic oil cavity and communicated with the hydraulic oil cavity, the cross section of the pressurization cavity is smaller than that of the hydraulic oil cavity, and the piston is arranged in the pressurization cavity.

5. The zero-strain soil pressure sensor according to claim 1, wherein the processor is arranged in the cavity.

* * * * *